US005578662A

United States Patent [19]
Bennett et al.

[11] Patent Number: 5,578,662
[45] Date of Patent: Nov. 26, 1996

[54] BIOABSORBABLE BRANCHED POLYMERS CONTAINING UNITS DERIVED FROM DIOXANONE AND MEDICAL/SURGICAL DEVICES MANUFACTURED THEREFROM

[75] Inventors: Steven L. Bennett, Southington; Ying Jiang, North Haven; Elliott A. Gruskin, Killingworth; Kevin M. Connolly, Hamden, all of Conn.

[73] Assignee: United States Surgical Corporation, Norwalk, Conn.

[21] Appl. No.: 477,098

[22] Filed: Jun. 7, 1995

Related U.S. Application Data

[63] Continuation-in-part of Ser. No. 278,898, Jul. 22, 1994.

[51] Int. Cl.$^6$ .......................... C08G 63/08; C08G 65/26; C08G 65/32
[52] U.S. Cl. ..................... 524/54; 525/408; 525/409; 525/411; 525/413; 525/415; 528/73; 528/76; 424/78.06; 424/426; 604/304
[58] Field of Search .................... 525/408, 409, 525/411, 413, 415; 528/73, 76; 524/54; 424/426, 78.06; 604/304

[56] References Cited

U.S. PATENT DOCUMENTS

| | | |
|---|---|---|
| 2,890,208 | 6/1959 | Young et al. . |
| 3,063,967 | 11/1962 | Schultz . |
| 3,169,945 | 2/1965 | Hostettler et al. . |
| 3,391,126 | 7/1968 | Baggett et al. . |
| 3,645,941 | 2/1972 | Snapp et al. . |
| 3,666,724 | 5/1972 | Hostettler . |
| 3,741,941 | 6/1973 | Ashe . |
| 3,795,701 | 3/1974 | Jenkins et al. . |
| 3,912,692 | 10/1975 | Casey et al. . |
| 4,052,988 | 10/1977 | Doddi et al. . |
| 4,080,969 | 3/1978 | Casey et al. . |
| 4,118,470 | 10/1978 | Casey et al. . |
| 4,440,789 | 4/1984 | Mattei et al. . |
| 4,503,216 | 3/1985 | Fagerburg et al. . |
| 4,624,256 | 11/1986 | Messier et al. . |
| 4,632,975 | 12/1986 | Cornell et al. . |
| 4,643,191 | 2/1987 | Bezwada et al. . |
| 4,663,429 | 5/1987 | Murai et al. . |
| 5,047,048 | 9/1991 | Bezwada et al. . |
| 5,076,807 | 12/1991 | Bezwada et al. . |
| 5,080,665 | 1/1992 | Jarrett et al. . |
| 5,085,629 | 2/1992 | Goldberg et al. . |
| 5,100,433 | 3/1992 | Bezwada et al. . |
| 5,225,521 | 7/1993 | Spinu .................... 525/413 |
| 5,266,323 | 11/1993 | Guthrie .................. 424/410 |
| 5,290,853 | 3/1994 | Regan .................... 528/73 |
| 5,334,626 | 8/1994 | Lin . |

FOREIGN PATENT DOCUMENTS

| | | |
|---|---|---|
| 482467 | 4/1992 | European Pat. Off. . |
| 887180 | 1/1962 | United Kingdom ......... 528/76 |

OTHER PUBLICATIONS

Storey et al. Bioabsorbable Composites. II=Nontoxic, L–lysine Based Poly(esterurethant) Matrix Composites, Polymer Composites, Feb., 1993, vol. 14, No. 1, pp. 17–25.

*Primary Examiner*—David Buttner

[57] ABSTRACT

Star polymers of soft segment forming monomers are useful in forming surgical devices. The star polymers can be endcapped with isocyanate, mixed with a filler and/or cross-linked. The polymer compositions are useful, for example, as fiber coatings, surgical adhesives or bone putty, or tissue growth substrate.

16 Claims, No Drawings

BIOABSORBABLE BRANCHED POLYMERS CONTAINING UNITS DERIVED FROM DIOXANONE AND MEDICAL/SURGICAL DEVICES MANUFACTURED THEREFROM

This is a continuation-in-part of copending application Ser. No. 08/278,898 filed Jul. 22, 1994.

BACKGROUND OF THE INVENTION

1. Technical Field

This disclosure relates generally to bioabsorbable polymer compositions. Specifically, this disclosure relates to highly branched or star polymers derived from monomers known to form absorbable polymers. The bioabsorbable polymer compositions are particularly useful in the manufacture of absorbable surgical devices such as sutures, staples clips, anastomosis rings, bone plates and screws, matrices for the sustained and/or controlled release of pharmaceutically active ingredients, etc., fabricated at least in part therefrom.

2. Background of Related Art

Polymers and copolymers of, and surgical devices made from, lactide and/or glycolide and/or related compounds are well-known. See, e.g., U.S. Pat. Nos. 2,668,162, 2,683,136, 2,703,316, 2,758,987, 3,225,766, 3,268,486, 3,268,487, 3,297,033, 3,422,181, 3,442,871, 3,463,158, 3,468,853, 3,531,561, 3,565,869, 3,597,449, 3,620,218, 3,626,948, 3,636,956, 3,736,646, 3,739,773, 3,772,420, 3,773,919, 3,781,349, 3,784,585, 3,792,010, 3,797,499, 3,839,297, 3,846,382, 3,867,190, 3,875,937, 3,878,284, 3,896,802, 3,902,497, 3,937,223, 3,982,543, 4,033,938, 4,045,418, 4,057,537, 4,060,089, 4,137,921, 4,157,437, 4,243,775, 4,246,904, 4,273,920, 4,275,813, 4,279,249, 4,300,565, and 4,744,365, U.K. Pat. or Appln. Nos. 779,291, 1,332,505, 1,414,600, and 2,102,827, D. K. Gilding et al., "Biodegradable polymers for use in surgery-polyglycolic/poly (lactic acid) homo- and copolymers: 1," *Polymer* Volume 20, pages 1459–1464 (1979), and D. F. Williams (ed.), *Biocompatibility of Clinical Implant Materials*, Volume II, chapter 9: "Biodegradable Polymers" (1981). All of the foregoing documents are hereby incorporated by reference.

In addition, other patents disclose surgical devices prepared from copolymers of lactide or glycolide and other monomers including caprolactone or trimethylene carbonate have been prepared. For example, U.S. Pat. No. 4,605,730 and U.S. Pat. No. 4,700,704 disclose copolymers of epsilon-caprolactone and glycolide useful in making surgical articles and particularly surgical sutures having low Young's modulus. In addition, U.S. Pat. No. 4,624,256 relates to the utilization of high molecular weight caprolactone polymers as coatings for surgical sutures, while U.S. Pat. No. 4,429,080 discloses surgical articles manufactured from triblock copolymers prepared from copolymerizing glycolide with trimethylene carbonate.

Polymers, copolymers and surgical devices made from ε-caprolactone and/or related compounds have also been described in U.S. Pat. Nos. 3,169,945, 3,912,692, 3,942,532, 4,605,730, 4,624,256, 4,643,734, 4,700,704, 4,788,979, 4,791,929, 4,994,074, 5,076,807, 5,080,665, 5,085,629 and 5,100,433.

Polymers derived in whole or in part from dioxanone are known. Homopolymers of p-dioxanone are described, e.g., in U.S. Pat. Nos. 3,063,967; 3,063,968; 3,391,126; 3,645,941; 4,052,988; 4,440,789; and, 4,591,630. Copolymers containing units derived from p-dioxanone and one or more other monomers that are copolymerizable therewith are described, e.g., in U.S. Pat. Nos. 4,243,775; 4,300,565; 4,559,945; 4,591,630; 4,643,191; 4,549,921; 4,653,497; 4,791,929; 4,838,267; 5,007,923; 5,047,048; 4,076,807; 5,080,665; and 5,100,433 and European Patent Application Nos. 501,844 and 460,428. Most of the known dioxanone-derived homopolymers and copolymers are indicated to be useful for the fabrication of medical and surgical devices such as those previously mentioned.

The properties of the bioabsorbable polymers may differ considerably depending on the nature and amounts of the comonomers, if any, employed and/or the polymerization procedures used in preparing the polymers. Aforementioned U.S. Pat. No. 4,838,267 discloses block copolymers derived from p-dioxanone and glycolide that exhibit a high order of initial strength and compliance but lose their strength rapidly after implantation in the body. Sutures made from the copolymers are said to be particularly useful in surgical procedures, such as plastic surgery or repair of facial wounds, where it is desirable for the suture to lose its strength rapidly.

SUMMARY

The general formula of the novel polymers described herein is:

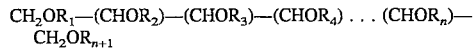

wherein: n equals 1 to 13, preferably 2 to 8 and most preferably 2 to 6;

$R_1, R_2 \ldots R_{n+1}$ are the same or different and selected from the group of a hydrogen atom or $(Z)_m$ wherein Z comprises repeating units selected from the group consisting of:

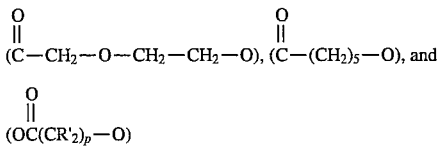

wherein p is 3 to 8 and each R' may be the same or different and are individually selected from the group consisting of hydrogen and alkyl having from 1 to 5 carbon atoms, such that at least three of said $R_1, R_2 \ldots R_{n+1}$ groups are other than hydrogen;

m is sufficient such that the star polymer has an inherent viscosity in HFPI at 25° C. between about 0.05 and about 0.5 dl/gm, preferably from about 0.15 to about 0.3 dl/gm, and most preferably from about 0.15 to about 0.2 dl/gm; and the m's for each (Z) group may be the same or different.

The polymers are initiated with a polyhydric alcohol. Preferred initiators are mannitol, pentaerythritol and threitol.

In a particularly useful embodiment, a bioabsorbable polymer of the foregoing general formula is provided wherein (Z) consists essentially of repeating units of the formula:

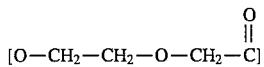

and the polymer has an inherent viscosity between about 0.05 and 0.5 dl/gram in HFIP at 25° C.

The polymers described herein are useful in the production of surgical devices. In particularly useful embodiments the polymers are used in coatings on surgical devices, such as, for example fibers used to produce sutures, meshes, woven structures, etc.

The polymers may be endcapped with an isocyanate. The isocyanate capped polymer may be cross-linked in the presence of water and/or a catalyst, such as tertiary amine catalyst. The cross-linked star polymers are useful for example as bone adhesives or bone fillers. Optionally, the polymer may be mixed with a filler such as hydroxyapatite or other bioceramic prior to cross-linking to produce a bone putty.

Alternatively, after endcapping with an isocyanate, a charge may be chemically induced on the polymer, such as, for example by reacting a fraction of the available isocyanate groups with diethylene ethanolamine (DEAE) and then cross-linking at least a portion of the balance of the remaining available isocyanate groups to form a water-insoluble, degradable, charged particle. These charged compositions are useful for example as an agent to enhance soft tissue wound healing.

DETAILED DESCRIPTION OF PREFERRED EMBODIMENTS

The general formula of the basic polymer in accordance with this disclosure is:

$$CH_2OR_1-(CHOR_2)-(CHOR_3)-(CHOR_4)\ldots(CHOR_n)-CH_2OR_{n+1}$$

wherein: n equals 1 to 13, preferably 2 to 8 and most preferably 2 to 6;

$R_1, R_2 \ldots R_{n+1}$ are the same or different and selected from the group of a hydrogen atom or $(Z)_m$ wherein Z comprises repeating units selected from the group consisting of:

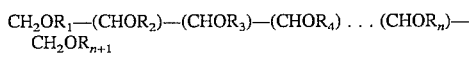

$$\begin{matrix} O & & O \\ \| & & \| \\ (C-CH_2-O-CH_2-CH_2-O), & (C-(CH_2)_5-O), \text{ and} \end{matrix}$$

$$\begin{matrix} O \\ \| \\ (OC(CR'2)_p-O) \end{matrix}$$

wherein p is 3 to 8 and each R' may be the same or different and are individually selected from the group consisting of hydrogen and alkyl having from 1 to 5 carbon atoms, such that at least three of said $R_1, R_2 \ldots R_{n+1}$ groups are other than hydrogen;

m is sufficient such that the star polymer has an inherent viscosity in HFPI at 25° C. between about 0.05 and about 0.5 dl/gm, preferably from about 0.15 to about 0.3 dl/gm; and most preferably from about 0.15 to about 0.2 dl/gm, and the m's for each Z group may be the same or different.

The purified monomer(s) used to form the Z groups are preferably dried and then polymerized at temperatures ranging from about 20° C. to about 130° C., preferably above 75° C., in the presence of an organometallic catalyst such as stannous octoate, stannous chloride, diethyl zinc or zirconium acetylacetonate. The polymerization time may range from 1 to 100 hours or longer depending on the other polymerization parameters but generally polymerization times of about 12 to about 48 hours are employed. In addition, a polyhydric alcohol initiator is employed to provide a highly branched or star structure. Any polyhydric alcohol may be employed, with mannitol ($C_6H_8(OH)_6$), pentaerythritol ($C(CH_2OH)_4$) threitol ($C_4H_6(OH)_4$) being preferred. Generally, the amount of initiator used will range from about 0.01 to about 15 percent by weight based on the weight of the monomer. Preferably, the initiator will be present in the reaction mixture in an amount from about 0.5 to about 5.0 weight percent based on the weight of the monomer.

The polymeric chains (Z groups) may be formed using any monomer known to form a bioabsorbable polymer, however, preferably monomers of the type know as soft segments forming polymers constitute the predominant component (i.e., constitute more than 50 mole percent) of the polymeric chains. Thus, for example, the polymeric chains may be formed predominantly from ε-caprolactone; alkylene carbonates such as trimethylene carbonate; substituted alkylene carbonates such as dimethyl trimethylene carbonate (DMTMC); and/or p-dioxanone. When the polymers of this invention are used without isocyanate endcapping (as described more fully hereinafter), homo- or copolymers of DMTMC and homopolymer of p-dioxanone are preferred.

Particularly useful polymers are those wherein the Z groups consist essentially of repeating units of the formula:

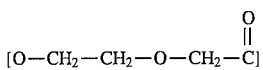

$$[O-CH_2-CH_2-O-CH_2-\overset{\overset{\displaystyle O}{\|}}{C}]$$

and can be prepared from monomer having the formula:

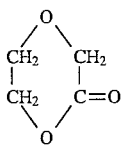

The monomer can be prepared using known techniques such as, for example, those processes described in U.S. Pat. Nos. 2,900,345; 3,119,840; 4,070,315 and 2,142,033, the disclosures of which are incorporated by reference. A preferred method of preparing the monomer is by dehydrogenating diethylene glycol in the presence of a copper/chromium catalyst.

The monomer should be purified, preferably to at least about 98 percent purity. The monomer may be purified using any known technique such as multiple distillations and/or recrystallizations. A preferred purification process is recrystallization from ethyl acetate as described in commonly owned application Ser. No. 08/036,922 filed Mar. 25, 1993, the disclosure of which is incorporated herein by reference.

An example of how polydioxanone star polymers are made employs the following steps:

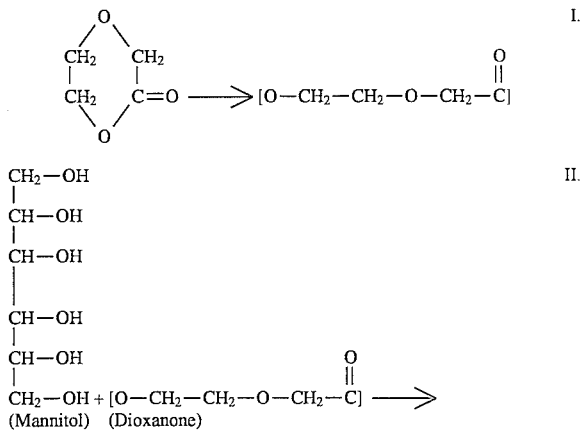

-continued

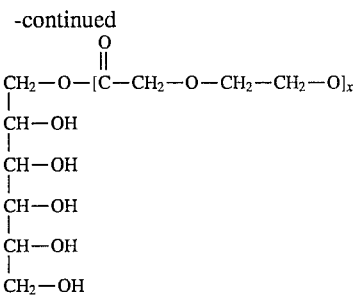

The product of step II further reacts until three or more hydroxy groups per molecule of mannitol have bound to a respective polydioxanone chain. To form the following polydioxanone star polymer:

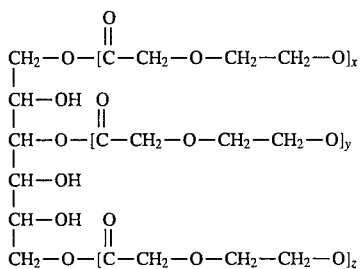

where the value of x, y and z for the polydioxanone chains may be the same or different so long as the product has an inherent viscosity between about 0.05 deciliters per gram and about 0.5 deciliters per gram in hexafluoroisopropanol (HFPI) at 25° C.

Polymers of p-dioxanone are not soluble in common organic solvents. An advantage of the polymer described herein is that it is soluble in methylene chloride. Thus it is easily used as a coating.

The polymerization parameters are controlled to provide a polymer having an inherent viscosity between about 0.05 and 0.5 dl/gram in HFIP at 25° C. It is within the purview of those skilled in the art to determine the appropriate polymerization parameters to provide polymers having the desired inherent viscosity in view of the disclosure herein.

The polymers described herein can be used as an absorbable coating for surgical devices formed from using any known technique, such as, for example, extrusion, molding and/or solvent casting. The polymers can be used alone, blended with other absorbable compositions, or in combination with non-absorbable components. A wide variety of surgical articles can be coated with the polymers. These include but are not limited to clips and other fasteners, staples, sutures, pins, screws, prosthetic device, wound dressings, drug delivery devices, anastomosis rings, and other implantable devices. Fibers coated with the present polymers can be knitted or woven with other fibers, either absorbable or nonabsorbable to form meshes or fabrics.

The star polymers described herein may advantageously be endcapped with isocyanate groups.

Isocyanate endcapping can be achieved by reacting the polymer with a diisocyanate. Suitable diisocyanates include hexamethylene diisocyanate, diisocyanatolysine ethyl ester and butane diisocyanate with diisocyanatolysine ethyl ester being preferred. Diisocyanates which may lead to harmful by-products upon hydrolysis of the polymer, such as, for example, certain aromatic diisocyanates, should not be employed where the composition is intended for use within a mammalian body. While endcapping with diisocyanate is preferred, it is also contemplated that other agents having at least two reactive sites can be employed for endcapping and for facilitating cross-linking. Suitable other endcapping agents include, for example diketene acetals such as bis-vinyl-2, 4, 8, 10-tetraoxyspiroundecane.

The conditions under which the polymer is reacted with the diisocyanate may vary widely depending on the specific polymer being end capped, the specific diisocyanate being employed, and the desired degree of end capping to be achieved. Normally, the polymer is dissolved in a solvent and added dropwise to a solution of the diisocyanate at room temperature with stirring. The amount of diisocyanate employed can range from about 2 to about 8 moles of diisocyanate per mole of polymer. Suitable reaction times and temperatures range from about 15 minutes to 72 hours or more at temperatures ranging from about 0° C. to 250° C.

Once endcapped with isocyanate, the polymers may advantageously be cross-linked. Cross-linking is normally performed by exposing the endcapped polymer to water in the presence of a catalyst, such as a tertiary amine catalyst.

The exact reaction conditions for achieving cross-linking will vary depending on a number of factors such as the composition of the polymer, the degree of endcapping, the specific isocyanate used to end cap and the desired degree of cross-linking. Normally, the cross-linking reaction is conducted at temperatures ranging from 20° C. to about 40° C. for five minutes to about 72 hours or more. The amount of water employed will normally range from about 0.05 moles to 1 moles per mole of polymer. While water is a preferred reactant to effect cross-linking it should be understood that other compounds could also be employed either together with or instead of water. Such compounds include diethylene glycol, polyethylene glycol and diamines, such as, for example, diethylamino propanediol. Suitable catalysts for use in the cross-linking reaction include 1,4 diazobicyclo [2.2.2] octane, triethylamine, and diethylaminoethanol.

The amount of catalyst employed can range from about 0.5 grams to about 50 grams per kilogram of polymer being cross-linked.

When the composition is intended for implantation it is possible to effectuate cross-linking in situ using the water naturally present in a mammalian body or with added water. However, to precisely control the conditions and extent of cross-linking, it is preferred to partially cross-link the polymer prior to its use as an implant.

The isocyanate endcapped polymers can also be cross-linked by the application of heat alone, or by exposing the polymer to diamine vapor. These cross-linking techniques are particularly useful when the polymers are to be used as a filament coating.

In an alternative embodiment, the isocyanate endcapped polymers described herein are admixed with a filler prior to cross-linking. While any known filler may be used, hydroxyapatite or other bioceramics are the preferred fillers. Normally, from about 10 grams to about 400 grams of filler are mixed with 100 grams of polymer. Cross-linking of the polymer/filler mixture can be carried out using any of the above-described methods. The filled, cross-linked polymers are useful, for example, as a molding composition. The filled polymers are stable for several weeks when kept dry. These dry mixtures will cross-link upon exposure to water without dispersing in water.

In another embodiment, an isocyanate endcapped star polymer is chemically altered to provide a desired charge on the polymer. The presence of charged groups on the polymer can enhance wound healing in either hard or soft tissue. To impart a positive charge, the endcapped polymer may be reacted with a positive charge inducing reactant. One suitable positive charge inducing reactant is diethylethanolamine which results in the presence of diethylaminoethyl (DEAE) groups on the polymer. To impart a negative charge, the endcapped polymer may be reacted with a negative charge inducing reactant. One such reactant is carboxymethanol which results in the presence of carboxymethyl (CM) groups on the polymer.

The conditions at which the charge inducing reactant is reacted with the isocyanate endcapped polymer will vary depending on the specific polymer, the degree of endcapping, the nature of the isocyanate used for endcapping and the number of charges to be provided on the polymer. Normally, from about 0.1 to about 0.5 moles of charge inducing reactant are employed per mole of isocyanate groups. The polymer is normally dissolved in a solvent and added dropwise to a solution of the charge inducing reactant. Stirring and heating to temperatures up to about 40° C. can facilitate the reaction.

In another embodiment, isocyanate endcapped star polymer and filler are first mixed together as disclosed hereinabove and thereafter charge inducing reactant is added to the mixture in the same manner as disclosed hereinabove. It has been found that these mixtures of isocyanate endcapped star polymer, filler and charge inducing reactant are stable for several weeks and more when stored under dry conditions.

It should be understood that for polymers of the embodiments having an induced charge and/or endcapped with a lysine isocyanate, any bioabsorbable polymer may be employed. Preferred bioabsorbable polymers according to this embodiment are those having the general formula:

$$CH_2O_1—(CHOR_3)—(CHOR_4)\ldots(CHOR_n)—CH_2OR_{n+1}$$

wherein: n equals 1 to 13; $R_1, R_2 \ldots R_{n+1}$ are the same or different and selected from the group of a hydrogen atom or Z wherein Z comprises repeating units selected from the group consisting of glycolide, lactide, p-dioxanone, ∈-caprolactone and alkylene carbonate units;

at least three of said $R_1, R_2 \ldots R_{n+1}$ groups being other than hydrogen;

at least one of said Z groups being endcapped with an isocyanate; and at least a portion of said endcapped Z groups having diethylamino ethyl group thereon.

Other suitable bioabsorbable polymers which may be endcapped with isocyanate include polyalkylene oxides containing a major amount, i.e., greater than 50 weight percent, of alkylene oxide units such as ethylene oxide units, propylene oxide units and combinations thereof and a minor amount, i.e., less than 50 weight percent, preferably less than about 20 weight percent, more preferably less than about 5 weight percent, units derived from a bioabsorbable monomer such as glycolide, lactide, glycolic acid, lactic acid, p-dioxanone, trimethylene carbonate, trimethylene dimethylene carbonate, dioxepanone, alkylene oxalates, epsilon-caprolactone, combinations of the foregoing, and the like. The polyalkylene oxides can be linear or branched random, block or graft copolymers. The polyalkylene oxides employed herein will generally be of low molecular weight, e.g., the polymer will possess a molecular weight of less than about 6,000.

It has also been discovered that novel polymers in accordance with this disclosure can serve as a substrate for cell growth. Specifically, star polymers endcapped with lysine diisocyanate, with or without an induced charge, can be used as a cell growth substrate.

In yet another embodiment, the isocyanate capped star polymer is reacted with an alkylene oxide polymer. In this manner, hydrophilic pendent chains are formed from at least a portion of the isocyanate groups on the polymer. Preferably, at least a portion of the isocyanate groups remain available for cross-linking. Suitable polyalkylene oxides include polyethylene oxide, polypropylene oxide and block copolymers of polyethylene oxide and polypropylene oxide. The alkylene oxide side chains reduce cell adherence while maintaining the biodegradability of the polymer.

It is further contemplated that one or more medico-surgically useful substances, e.g., those which accelerate or beneficially modify the healing process when particles are applied to a surgical repair site, can be incorporated into surgical devices made from the materials described herein. So, for example, the surgical device can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamicin sulfate, erythromycin or VX glycopeptides) which are slowly released into the tissue can be applied in this manner to aid in combating clinical and sub-clinical infections in a tissue repair site. To promote repair and/or tissue growth, one or several growth promoting factors can be introduced into the sutures, e.g., fibroblast growth factor bone morphogenetic protein, epidermal growth factor, platelet derived growth factor, macrophage derived growth factor, alveolar derived growth factor, monocyte derived growth factor, magainin, and so forth. Some therapeutic indications are: glycerol and tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system. It is also contemplated that the medico-surgically useful substance may enhance blood coagulation. Thrombin is one such substance.

It is further contemplated that the isocyanate capped polyalkylene oxide polymer described above can be combined with therapeutic agents, preferably charged oxidized beads, e.g., cross-linked dextran, which are commonly employed to promote wound healing. The above mixture of hydrophilic isocyanate capped polyalkylene oxide and therapeutic agent can be reacted with any of the above-identified isocyanate capped star polymers prior to introduction to the wound site to form a polymer network that entraps the therapeutic agent. Upon placement of the polyalkylene oxide/isocyanate capped star polymer network in the wound, the liquid present at the wound site causes the polymer network to swell; thereby allowing delivery of the therapeutic agent through either diffusion or degradation of the polymer network.

The following non-limiting Examples illustrate the preparation of polymers in accordance with the present disclosure.

EXAMPLES 1–3

100.0 grams of purified p-dioxanone (99.5% purity) is placed in a polymerization tube. Then 0.02% (w/w) Sn(Oct)$_2$, i.e., weight of Sn(Oct)$_2$ to weight of polydioxanone, in diethyl ether is added to the tube and dried for two hours under vacuum at 25° C. In addition, the following amounts of the indicated initiator is added to the vessel:

| Example No. | Initiator | Amount |
| --- | --- | --- |
| 1 | Mannitol | 1.0 gram |
| 2 | Mannitol | 2.0 grams |
| 3 | Threitol | 2.0 grams |

Polymerization is conducted at 100° C. for 24 hours. The resulting polymer is heated to 75° C. at reduced pressure (0.5 mmHg) to remove any residual monomer or other volatile impurities. The polymers produced have the following inherent viscosities in HFIP at 25° C.:

| Example No. | Inherent Viscosity |
|---|---|
| 1 | 0.83 |
| 2 | 0.77 |
| 3 | 0.39 |

EXAMPLES 4–7

75 grams of p-dioxanone (99.5%=purity) is placed in a polymerization tube. Then, 0.015% (w/w) $Sn(Oct)_2$, i.e., weight of $Sn(Oct)_2$ to weight of polydioxanone, in diethyl ether is added to the tube and dried for two hours under vacuum at 25° C. In addition, the following amounts of the indicated initiator is added to the vessel:

| Example No. | Initiator | Amount |
|---|---|---|
| 4 | Mannitol | 1.0 gram |
| 5 | Mannitol | 0.5 grams |
| 6 | Threitol | 1.5 grams |
| 7 | Threitol | 0.75 grams |

Polymerization is conducted for 24 hours at 100° C. The resulting polymers are particularly useful for coatings on braided absorbable sutures.

EXAMPLE 8

A star copolymer of p-dioxanone and glycolide is prepared as follows: 458.3 grams of previously dried p-dioxanone, 41.7 grams of previously dried glycolide, 147.5 grams of mannitol, and 0.106 grams of stannous octoate catalyst are reacted in a $N_2$ atmosphere under anhydrous conditions in a one liter 3 neck flask equipped with a mechanical stirrer.

The flask is heated overnight at 98° C. with stirring at 60 rpm. The mixing rate is increased to 100 rpm after about 12 hours of reaction. After 20 hours, the temperature is reduced to 90° C. The stirring rate is further increased to 200 rpm after a total of 22 hours of reaction time. After a total reaction time of about 39 hours, the material is extruded at 94°±4° C. The flask is placed under vacuum for 6 hours and the polymer is post-treated by heating at 75° C. for about 63 hours. A total weight of 599.5 grams of polymer is recovered.

The following non-limiting Examples illustrate the end-capping of polymers in accordance with this invention:

EXAMPLE 9

Preparation of Star Copolymer

A star copolymer of p-dioxanone and glycolide is prepared as follows: 458.3 grams of previously dried p-dioxanone, 41.7 grams of previously dried glycolide, 83.5 grams of pentaerythritol, and 0.106 grams of stannous octoate catalyst are reacted in a $N_2$ atmosphere under anhydrous conditions in a one liter 3 neck flask equipped with a mechanical stirrer. Polymerization is conducted at 90° C. with stirring for a total reaction time of about 69 hours. The copolymer is then extruded and heated at 135° C. for 72 hours to remove vaporizable impurities.

Preparation of Lysine Diisocyanate Compound

A five 1 round bottom flask equipped with a mechanical stirrer, condenser and thermometer is dried by heating to>100° C. under nitrogen purge. After cooling the reactor is charged with 500.0 g lysine ethyl ester dihydrochloride (I) and 4000 ml 1,1,1,3,3,3-hexamethyl disilazane (II). The slurry is heated to 117° C. for 24 hours, cold and filtered through Celite to remove the silazane hydrochloride salt. After filtration excess disilazane (II) is removed under vacuum at room temperature leaving a clear light pink liquid (III). This product is purified by distillation at <50 mT. 325 ml of a light yellow liquid is obtained between 120° and 130° C. (Yield: 295 g, 48%.)

A five-liter round bottom flask equipped with a mechanical stirrer, 1 liter addition funnel and thermometer is dried by heating to>100° C. under nitrogen purge. After cooling the reactor is charged with 2500 ml anhydrous ether, 245 ml triethyl amine and 317 ml of the previously obtained reaction product (III). In a separate dry flask 189 g of triphosgene is combined with 1250 ml of ether and stirred under nitrogen until a clear solution is obtained. This solution is transferred to the addition funnel and added dropwise to the solution in the flask at −20° C. After the addition is complete the reaction is allowed to warm to room temperature and stirred for 40 hrs. At the end of this time the solution is filtered to remove the TEA hydrochloride salt and placed on the rotovap to reduce the volume. A simple distillation at<200 mT results in a purified product received between 107 and 110° C. The clear, colorless liquid weights 125 g, (60% yield). The total yield is 29%.

The reaction sequence can be schematically represented as follows

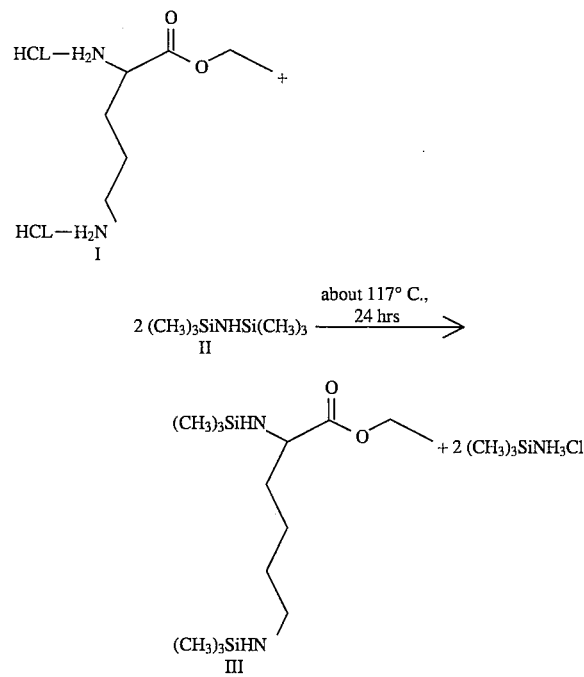

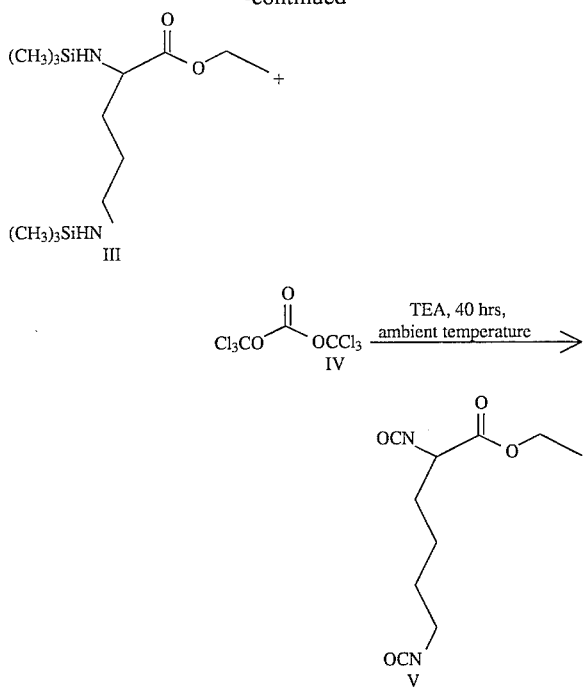

Preparation of Lysine Isocyanate Endcapped Polymer

A 500 ml round bottom flask is dried by heating under a nitrogen purge. 57.6 grams of the lysine diisocyanate prepared as described above and 28.6 grams of the star dioxanone/glycolide copolymer are added to the flask. The reactants are heated to and maintained at 60° C. for six hours. 82 grams of lysine isocyanate endcapped polymer are obtained.

EXAMPLE 10

A star copolymer of dioxanone and caprolactone is prepared by reacting 250 grams of p-dioxanone with 250 grams ε-caprolactone and 36 grams of mannitol in the presence of a stannous actuate catalyst at 135° C. for 72 hours. The resulting polymer is then heated at 75° C. overnight. 25 grams of the polymer is dissolved in 125 ml of methylene chloride. Hexamethylene diisocyanate (25 ml) is mixed with 50 ml of methylene chloride. The hexamethylene diisocyanate solution is added dropwise to the polymer solution with stirring. The reaction mixture is maintained at the boil with continuous stirring overnight (about 24 hours). The resulting endcapped polymer is the precipitated in hexane and recovered by decanting the solvent. Excess solvent is removed by evaporation.

EXAMPLE 11

A homopolymer of DMTMC is prepared by placing 500 grams DMTMC in a reactor with 14 grams of pentaerythritol initiator and 0.01 grams of stannous octoate catalyst. Polymerization is allowed to occur at 150° C. for 24 hours. The resulting polymer is heated at 90° C. and >0.5 mmHg for 48 hours to remove residual monomer and other volatile impurities.

45 grams of the DMTMC polymer is dissolved in 50 ml methylene chloride and is added dropwise to 100 grams hexamethylene diisocyanate. The mixture is stirred at room temperature for 48 hours. The resulting endcapped DMTMC polymer is washed twice with hexane and dried.

The following Example illustrates the use of the cross-linked polymers as a coating for sutures.

EXAMPLE 12

Five grams of the endcapped polymer of Example 9 are dissolved in 100 ml of methylene chloride. The polymer solution is applied to an absorbable monofilament suture. The coated suture is heated to simultaneously drive off solvent and effectuate cross-linking of the polymer coating. The monofilament coated in this manner exhibits greater in vivo strength retention compared to uncoated monofilaments of the same size and composition.

The following Examples show filled cross-linked polymers useful as a bone-putty.

EXAMPLE 13

Ten grams of the isocyanate endcapped polymer of Example 9 is mixed with 5 grams of hydroxyapatite. Once a substantially homogenous mixture is attained, the polymer is cross-linked by the addition of 0.5 ml of water, 1 ml of DEAE and 0.5 ml stannous octoate. As the reaction proceeds, $CO_2$ is released, forming a moldable foam which has a putty-like consistency and can be molded by hand into a desired shape or easily packed into a bone defect.

EXAMPLES 14–18

10 grams of isocyanate endcapped star copolymer of Example 9 is mixed with 5.0 grams of hydroxyapatite until a substantially homogeneous mixture is obtained in the form of a white paste. Various formulations of bone putty are produced by adding water, stannous octoate, and diethylethanolamine to 1.0 gram of the hydroxyapatite/endcapped star copolymer paste. These formulations are presented in the following table:

| Example No. | Hydroxyapatite Copolymer of Ex. 9 | $H_2O$ | $Sn(Oct)_2$ | DEAE | Increase in Volume |
|---|---|---|---|---|---|
| 14 | 1.0 gram | 1 drop | 2 drops | 2 drops | 2X |
| 15 | 1.0 gram | 1 drop | 2 drops | 3 drops | 3X |
| 16 | 1.0 gram | 1 drop | 3 drops | 3 drops | 3X |
| 17 | 1.0 gram | 1 drop | 3 drops | 2 drops | 4X |
| 18 | 1.0 gram | 1 drop | 4 drops | 7 drops | 2X |

Each formulation hardens to provide structural support to aid in hard tissue healing. The bone putty of Examples 18–20 becomes hard to the touch in 10 minutes or less.

EXAMPLE 19

A modified bone putty is prepared as follows: 6.1 grams of calcium phosphate tribasic are mixed with 3.2 grams of hydroxyapatite. 15 grams of endcapped star copolymer of Example 10 are added to the calcium phosphate tribasic/hydroxyapatite mixture.

1.0 gram of the endcapped star copolymer/calcium phosphate tribasic/hydroxyapatite composition is placed into a scintillation vial. Two drops of a 2:1 diethylethanolamine/$H_2O$ mixture and 2 drops of $Sn(Oct)_2$ catalyst solution are added to the vial. The resulting composition is placed into a tibia bone defect, where it foams with the release of $CO_2$, absorbs blood and hardens to provide structural support to the bone.

The following Examples show the use of the present polymer as a substrate for cell growth.

EXAMPLES 19–23

The endcapped polymer of Example 9 is mixed with various amounts of DEAE solution as set forth in the following Table:

| Example No. | Polymer (gms) | DEAE (drops) | Concentration DEAE (grams/drop) |
| --- | --- | --- | --- |
| 19 | .35 | 0 | N/A |
| 20 | .33 | 5 | .07 |
| 21 | .31 | 3 | .10 |
| 22 | .42 | 2 | .21 |
| 23 | .27 | 1 | .027 |

The polymers are coated onto one half of a 5 cm tissue culture plate and allowed to cure for two days. Mouse fibroblasts (L929) are trypsinized and seeded onto the plates. The cells are grown in minimal essential media with 10 % fetal calf serum. The medium was changed after 1,4 and 7 days. Cell growth was observed on both the uncoated and coated half of the tissue culture plate, indicating that the present polymers are a suitable substrate for cell growth.

The following Example shows the preparation of a polymer of another embodiment.

EXAMPLE 24

10 grams of the lysine isocyanate capped polymer of Example 9 are placed into a reaction vessel with 9 grams of poly(ethylene oxide monomethylether) (Mol. Wt. 350) and 0.0038 grams stannous octoate. The reactants are stirred at ambient temperature for 4 hours. The resulting polymer is recovered as a viscous liquid which can be applied directly to a wound site.

EXAMPLE 25

20.6 g of diisocyanatolysine ethyl ester was placed in a clean, dry 100mL round bottomed flask equipped with stirrer and $N_2$ flow. The material was allowed to dry. A 95:5 weight percent polyethyleneoxide-glycolide copolymer (1000 molecular weight) was placed under vacuum for about 1 hour. The polymer was then added dropwise to the diisocyanatolysine ether ester via syringe to provide an isocyanate-endcapped material.

It will be understood that various modifications may be made to the embodiments disclosed herein. For example, the compositions in accordance with this disclosure can be blended with other biocompatible, bioabsorbable or non-bioabsorbable materials. Therefore, the above description should not be construed as limiting, but merely as exemplifications of preferred embodiments. Those skilled in art will envision other modifications within the scope and spirit of the claims appended hereto.

What is claimed is:

1. A bioabsorbable composition comprising a branched copolymer containing a major amount of alkylene oxide units and a minor amount of units derived from a bioabsorbable monomer, said copolymer being endcapped with at least one lysine isocyanate group.

2. The composition of claim 1 wherein the alkylene oxide units are selected from the group consisting of ethylene oxide, propylene oxide and combinations thereof.

3. The composition of claim 1 wherein the bioabsorbable monomer is selected from the group consisting of glycolic acid, glycolide, lactic acid, lactide, p-dioxanone, trimethylene carbonate, trimethylene dimethylene carbonate, dioxepanone, alkylene oxalates, epsilon-caprolactone, and combinations thereof.

4. The composition of claim 1 wherein the units derived from a bioabsorbable monomer represent about 20 weight percent of the copolymer.

5. The composition of claim 1 wherein the units derived from a bioabsorbable monomer represent about 5 weight percent of the copolymer.

6. The composition of claim 1 wherein the copolymer is linear or branched.

7. The composition of claim 1 wherein the copolymer is a random, block or graft copolymer.

8. The composition of claim 1 wherein the copolymer possesses a molecular weight of less than about 6,000.

9. The composition of claim 1 wherein the isocyanate group is derived frown diisocyanatolysine ethyl ester.

10. The composition of claim 1 wherein the bioabsorbable monomer is selected from the group consisting of glycolic acid, glycolide, lactic acid and lactide.

11. The composition of claim 1 further comprising a filler.

12. The composition of claim 1 further comprising a charge inducing agent.

13. The composition of claim 1 further comprising a therapeutic agent.

14. The composition of claim 13 wherein the therapeutic agent is cross-linked dextran.

15. A method for promoting wound healing which comprises contacting a wound site with the bioabsorbable composition of claim 13.

16. A bioabsorbable composition comprising a branched copolymer containing a major amount of alkylene oxide units and a minor amount of units derived from a bioabsorbable monomer selected from the group consisting of glycolic acid, glycolide, lactic acid, lactide, p-dioxanone, trimethylene carbonate, trimethylene dimethylene carbonate, dioxepanone alkylene oxalates, epsilon-caprolactone, and combinations thereof, said copolymer being endcapped with at least one isocyanate group derived from diisocyanatolysine ethyl ester.

* * * * *